United States Patent [19]

Park et al.

[11] Patent Number: 5,670,546
[45] Date of Patent: Sep. 23, 1997

[54] N-ARYLALKYLPHENYLACETAMIDE DERIVATIVES

[75] Inventors: No-Sang Park; Young-Sik Jung; Churl-Min Seong; Jong-Cheol Lee; Jin-Il Choi, all of Daejeon; Seung-Won Choi, Seoul; Yeon-Joo Choi; Kwang-Sook Lee, both of Daejeon, all of Rep. of Korea

[73] Assignee: Korean Research Institute of Chemical Technology, Seoul, Rep. of Korea

[21] Appl. No.: 584,025

[22] Filed: Jan. 11, 1996

[30] Foreign Application Priority Data

Jan. 10, 1995 [KR] Rep. of Korea ............ 95-299

[51] Int. Cl.$^6$ ................... A61K 31/165
[52] U.S. Cl. ............ 514/620; 514/622; 514/539; 514/551; 514/255; 514/428; 544/398; 544/399; 548/562; 560/27; 564/164; 564/165; 564/167; 564/170
[58] Field of Search .............. 514/620, 622, 514/539, 551, 255, 428; 564/164, 165, 167, 170; 544/398, 399; 548/562; 560/27

[56] References Cited

U.S. PATENT DOCUMENTS

| | | | |
|---|---|---|---|
| 4,562,201 | 12/1985 | Stout et al. | 512/622 |
| 4,983,633 | 1/1991 | Itol et al. | 514/622 |
| 5,013,759 | 5/1991 | Berman et al. | 514/622 |
| 5,135,949 | 8/1992 | van der Saal et al. | 514/622 |
| 5,242,944 | 9/1993 | Park et al. | 514/466 |
| 5,430,060 | 7/1995 | Brittain et al. | 514/622 |

OTHER PUBLICATIONS

Korean J. of Med. Chem., vo. 1, No. 1, 1991 pp. 36-43, No-Sang Park, at al.

Park et al, Chem. Abst, vol. 117, #48,051d (1992).

Kissei, Chem. Abst, vol. 96, #180,994r (1982).

*Primary Examiner*—James H. Reamer
*Attorney, Agent, or Firm*—Anderson Kill & Olick P.C.

[57] ABSTRACT

N-arylalkylphenylacetamide compounds of formula (I), and pharmaceutically acceptable salts thereof, possess potent analgesic and anti-inflammatory activities.

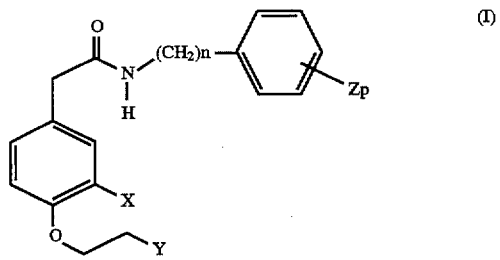

4 Claims, No Drawings

N-ARYLALKYLPHENYLACETAMIDE DERIVATIVES

FIELD OF THE INVENTION

The present invention relates to N-arylalkylphenylacetamide derivatives which have powerful analgesic and anti-inflammatory activities and pharmaceutically acceptable salts thereof.

BACKGROUND OF THE INVENTION

Capsaicin(trans-8-methyl-N-vanillyl-6-nonenamide), which is contained in the fruit juice of a plant belonging to the genus Capsicum, has been known to possess an analgesic activity. Derivatives of such natural capsaicin as well as synthetic capsaicin (N-vanillyl-nonan-amide) have been described as analgesia(see LaHann, U.S. Pat. No. 4,313,958, LaHann et al., U.S. Pat. No. 4,424,205 and Gardner et al., EP Patent No. 0,282,177).

These compounds are, however, generally known to have various side-effects: for example, strong irritation, reddening of skin and toxicity.

Also reported are 4-(2-aminoethoxy)phenylacetamide derivatives as having high pharmacologic and physiologic activities(see Park et al., U.S. Pat. No. 5,242,944). However, they still have low oral bioavailability and they still exhibit some of the skin irritation and toxic properties.

SUMMARY OF THE INVENTION

It is, therefore, a primary object of the present invention to provide a N-arylalkylphenylacetamide compound having excellent analgesic and anti-inflammatory activities, increased oral bioavailability and a greatly reduced level of skin irritation and toxicity.

It is another object of the present invention to provide a pharmaceutical composition containing the compound as an active ingredient.

In accordance with the present invention, there is provided a N-arylalkylphenylacetamide compound of the following formula (I) and pharmaceutically acceptable salts thereof:

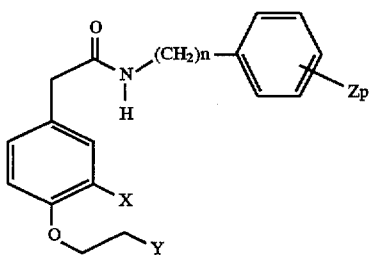

wherein:

X is a hydrogen, halogen, hydroxy or methoxy group;

Y is OR wherein R is a hydrogen, $C_{1-3}$ hydroxyalkyl or $C_{1-3}$ aminoalkyl; or $NR^1R^2$ wherein $R^1$ and $R^2$, which may be the same or different, are independently a hydrogen, $C_{1-3}$ alkyl, $C_{1-3}$ hydroxyalkyl, $C_{1-3}$ aminoalkyl, formyl, $C_{1-3}$ alkylcarbonyl, $C_{1-3}$ alkoxycarbonyl, arylalkoxycarbonyl, aryl or aroyl group, with the proviso that both $R^1$ and $R^2$ are not simultaneously a hydrogen, or $R^1$ and $R^2$ may form a heterocyclic ring containing one or more heteroatoms together with a nitrogen atom to which they are attached;

Z, which may be the same or different when p is greater than 1, is a hydrogen, halogen, hydroxy, methylenedioxy, or trifluoromethyl group, or $R^3$ or $OR^3$ wherein $R^3$ is a $C_{1-5}$ alkyl, $C_{3-7}$ cycloalkyl, phenyl or benzyl group;

n is an integer ranging from 2 to 5; and p is 0 or an integer ranging from 1 to 5.

The compound of formula(I) of the present invention may form salts when Y contains one or more amino groups. Pharmaceutically acceptable salts thereof may be the salts of inorganic acids such as hydrochloric acid, hydrogen bromide, sulfuric acid, sodium hydrogen sulfate and carbonic acid, or of organic acids such as formic, acetic, oxalic, benzoic, citric, tartaric, gluconic, gentisic, fumaric, lactobionic, salicylic and acetylsalicylic acids. In addition, the compound of formula(I) of the present invention and pharmaceutically acceptable salts thereof may exhibit polymorphism.

In accordance with the present invention, there is also provided a pharmaceutical composition containing the compound of formula(I) as an active ingredient.

DETAILED DESCRIPTION OF THE INVENTION

A N-arylalkylphenylacetamide compound of formula (I) of the present invention may be prepared in accordance with the process which comprises the steps of: (i) reacting a compound of formula (II):

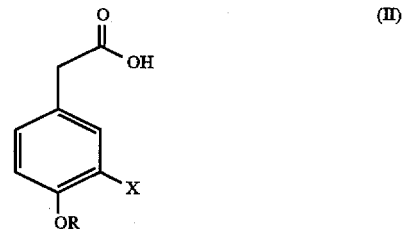

with an amine compound of formula (III):

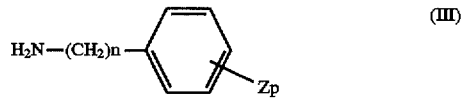

to provide a compound of formula (IV):

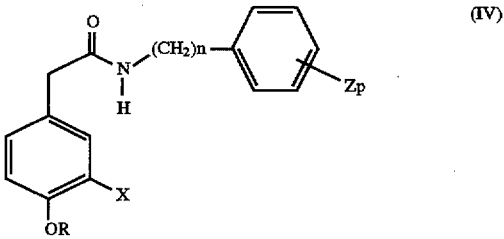

wherein X, Y, Z, n and p have the same meanings as defined as above, and R is $CH_2CH_2Cl$, $CH_2CH_2Br$, $CH_2CH_2N_3$ or $CH_2CH_2NH_2$; and (ii) reacting the compound of formula (IV) with a compound suitable for constructing a desired substituent Y to provide the compound of formula (I).

In the above process, reaction step (i) may be conducted, for example, in the presence of a condensing agent such as dicyclohexylcarbodiimide (DCC), by stirring an acetonitrile or dimethylformamide solution containing a compound of formula(II), a compound of formula(III) and a condensation agent in a molar ratio of ranging from 1:1:1 to 1:1:1.5 at a room temperature for 30 minutes to 24 hours, preferably 1 to 7 hours.

Alternatively, reaction step(i) may be conducted in the presence of a catalyst such as 3 Å, 4 Å or 5 Å, preferably powdered 4 Å molecular sieve, without the use of any solvent, for example, by heating a compound of formula(II) and a compound of formula(III) in a molar ratio of ranging from 1:1 to 1:1.5 at a temperature ranging from 120° to 170° C. for 1 to 24 hours, and preferably at a temperature ranging from 140° to 160° C. for 2 to 5 hours.

In reaction step(ii), the group R is reacted with a suitable compound to obtain the compounds of formula(I) having the desired Y group by any conventional method.

For example, a carbamate group may be introduced by stirring a mixture of a compound of formula(IV), wherein R is $CH_2CH_2NH_2$, and an appropriate chloroformate compound in a molar ratio ranging from 1:1 to 1:2 in dichloromethane for 1 to 5 hours at a room temperature; and other groups may be easily introduced by employing any conventional method as is described in more detail in the Examples thereof.

The compound of formula(II), which is used as a starting material in preparing the compound of formula(I) of the present invention, is commercially available and the amine compound of formula(III) may be obtained from a compound of the formula(V) by employing any conventional method, e.g., a reduction method described in U.S. Pat. No. 5,242,944, which employs alane, an alanate(e.g., lithium aluminium hydride) and the like:

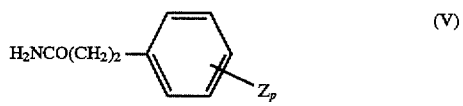

(V)

wherein, Z and p have the same meanings as defined as above.

Specifically, representative examples of the N-arylalkylphenylacetamide derivatives of formula(I) of the present invention are as follows:

N-{3-(3,4-dimethylphenyl)propyl}-4-(2-hydroxyethoxy)-3-methoxyphenylacetamide;

N-{3-(3,4-dimethylphenyl)propyl}-4-[2-{N-(2-hydroxyethyl)}-aminoethoxy]-3-methoxyphenylacetamide;

N-{3-(3,4-dimethylphenyl)propyl}-4-[2-{N,N-di(2-hydroxyethyl)}-aminoethoxy]-3-methoxyphenylacetamide;

N-{3-(3,4-dimethylphenyl)propyl}-4-[2-{N-(2-aminoethyl)}aminoethoxy]-3-methoxyphenylacetamide;

N-{3-(3,4-dimethylphenyl)propyl}-4-(2-piperazinylethoxy)-3-methoxyphenylacetamide;

N-{3-(3,4-dimethylphenyl)propyl}-4-(2-ethylformamido)-3-methoxyphenylacetamide;

N-{3-(3,4-dimethylphenyl)propyl}-4-{2-(N-benzyloxycarbonyl)-aminoethoxy}-3-methoxyphenylacetamide;

N-{3-(3,4-dimethylphenyl)propyl}-4-(2-methylaminoethoxy)-3-methoxyphenylacetamide;

N-{3-(3,4-dimethylphenyl)propyl}-4-{2-(1-pyrrolidinyl)ethoxy}-3-methoxyphenylacetamide;

N-{3-(3,4-dimethylphenyl)propyl}-4-{2-(N-ethyloxycarbonyl)aminoethoxy]-3-methoxyphenylacetamide; and N-{3-(3,4-dimethylphenyl)propyl}-4-[2-{N-(2-acetoxybenzoyl)}-aminoethoxy]-3-methoxyphenylacetamide.

The present invention also includes within its scope pharmaceutical compositions comprising one or more of the N-arylalkylphenylacetamide derivatives of formula(I) as active ingredients, in association with a possible pharmaceutically acceptable carrier. The term "(pharmaceutical) carrier", as used herein, means one or more compatible solid or liquid filler, diluents or encapsulating materials which are suitable for human or animal administration. The compatible carriers, as used herein, are the components that do not cause any interactions which substantially reduce the efficacy of the pharmaceutical composition in an ordinary user environment. Possible pharmaceutical carriers must be of sufficiently low toxicity to make them suitable for administration to the subject of treatment.

Some examples of substances which can serve as the carrier are sugar, starch, cellulose and its derivatives, powered tragacanth, malt, gelatin, talc, stearic acid, magnesium stearate, calcium sulfate, vegetable oils, polyols, alginic acid, pyrogen-free water, isotonic saline phosphate buffer solutions, cocoa buffer(suppository base), emulsifier as well as other non-toxic pharmaceutically compatible substances used in other pharmaceutical formulations. Wetting agents and lubricants such as sodium lauryl sulfate, as well as coloring agents, flavoring agents, excipients, tabletting agents, stabilizers, antioxidants and preservatives may also be present. Other compatible additives and ingredients such as pain killers, muscle relaxants may be included in the possible pharmaceutical carrier for use in the compositions of the present invention.

The proper pharmaceutical carriers of the present invention are basically determined by the administration route. The compounds of the present invention may be administered by injection, orally and topically. If the compound is to be injected, the preferred carrier is the sterile, physiological saline with pH 4. If the compound is to be applied topically, the carrier may preferably comprise those suited for use in creams, gels, tapes and the like. And the pharmaceutical carriers for oral administration may include those suited for tablets and capsules.

The carrier may comprise, in total, from about 0.1% to about 99.99999% by weight of the pharmaceutical compositions of the present invention, mainly from about 50% to about 99.9999%.

Total single dosages of the compounds of the present invention are generally from about 1 μg to about 10 g. Preferred single dosages are from about 1 μg to about 3500 mg; and more preferred are from about 1 μg to 1000 mg; and most preferred are from about 1 μg to about 600 mg.

Possible pharmaceutical carriers suitable for the preparation of unit dosage forms for oral administration and injection, and dosage forms for topical application are well-known in the art. Their selection may further depend on secondary considerations such as taste, cost, and/or shelf stability, which are not critical for the purposes of the present invention; and may be made without difficulty by a person skilled in the art.

The following Examples and Tests are intended to illustrate the present invention more specifically, without limiting the scope of the invention.

The terms and abbreviations used in the Examples have their normal meaning unless otherwise designated, for example, "° C." refers to degrees Celsius; "N" refers to normal or normality; "mmol" refers to millimole; "g" refers to gram; "ml" means milliliter; "M" refers to molar and "NMR" refers to nuclear magnetic resonance.

Unless otherwise specified, percentages or ratios given below for solids in solid mixtures, liquids in liquids and solids in liquids are on a w/w, v/v and w/v basis, respectively.

EXAMPLE 1

Synthesis of N-{3-(3,4-dimethylphenyl)propyl}-4-(2-hydroxyethoxy)-3-methoxyphenylacetamide Step 1)

Synthesis of 3-(3,4-dimethylphenyl)propionic acid

To a solution of 70.0 ml of diethyl malonate dissolved in 400 ml of dry ethanol was added 10.0 g of metallic sodium. The reaction mixture was stirred for 30 minutes and cooled to 0° C; and 66.5 g of 3,4-dimethylbenzyl chloride was added thereto. This reaction mixture was stirred at a room temperature for another 1 hour, heated at the boiling temperature for 4 hours and concentrated under a reduced pressure. The residue was dissolved in ethyl ether and the solution was washed with water. After further concentration under a reduced pressure, the organic phase was combined with 500 ml of water and 170 g of KOH; and this mixture was heated at the boiling temperature for 24 hours. The mixture was concentrated under a reduced pressure to about one half volume; then 200 ml of 98% sulfuric acid was added slowly thereto. The resultant solution was heated at the boiling temperature for 24 hours, extracted twice with 300 ml of ethyl acetate. The organic solvent was distilled off under a reduced pressure and the residue was recrystallized from boiling hexane to obtain 42.1 g of the title compound as a white solid(yield: 55%).

m.p.: 82° C.

$^1$HNMR(300 MHz, CDCl$_3$) δ2.22(s, 3H, CH$_3$), 2.24(s, 3H, CH$_3$), 2.66(t, J=8 Hz, 2H, ArCH$_2$), 2.89(t, J=8 Hz, 2H, CH$_2$CO), 6.93–7.70(m, 3H, ArH)

Step 2)

Synthesis of 3-(3,4-dimethylphenyl)propylamine

A mixture of 18.5 g of the compound obtained in step 1 and 50 ml of thionyl chloride was refluxed for 2 hours, concentrated under a reduced pressure and the residue was dissolved in 100 ml of ethyl ether. The resulting solution was added to a mixture of 200 ml of ethyl ether, 150 ml of water and 50 ml of 30% aqueous ammonia solution with stirring. The organic layer was discarded and the remaining aqueous layer was extracted twice with 150 ml of dichloromethane. The organic solvent was distilled off to obtain a residue which was essentially 3-(3,4-dimethylphenyl)propionamide. This residue dissolved in 150 ml of tetrahydrofuran was added to a mixture of 8.0 g of LiAlH$_4$ and 200 ml of tetrahydrofuran. The resultant mixture was refluxed for 5 hours; then 30 ml of 30% aqueous NaOH solution and 20 ml of water were added thereto. After separating the tetrahydrofuran layer, the solid residue was dissolved in 300 ml of water and extracted twice with 200 ml of ethyl ether. The tetrahydrofuran layer and the ethyl ether extract were combined, and the resulting solution was concentrated under a reduced pressure. The residue so obtained was distilled under a reduced pressure(140° to 150° C., 0.5 mmHg) to obtain 13.4 g of the title compound(yield: 79%).

$^1$H NMR(300 MHz, CDCl$_3$) δ1.32(br s, 2H, NH$_2$), 1.74 (quint, J=7 Hz, 2H, CH$_2$), 2.23(s, 3H, CH$_3$), 2.24(s, 3H, CH$_3$), 2.59(t, J=7 Hz, 2H, ArCH$_2$), 2.72(t, J=7 Hz, 2H, CH$_2$CN), 6.91–7.06(m, 3H, ArH)

Step 3)

Synthesis of N-{3-(3,4-dimethylphenyl)propyl}-4-hydroxy-3-methoxyphenylacetamide 1.39 g of the compound obtained in the step 2 was reacted with 1.50 g of 4-hydroxyl-3-methoxyphenylacetic acid in the presence of 0.60 g of powdered 4 Å molecular sieve by stirring at a temperature ranging from 150° to 160° C. for 4 hours. The reaction product was dissolved in 10 ml of dichloromethane and subjected to column chromatography to obtain 2.43 g of the title compound(yield: 90%).

$^1$H NMR(200 MHz, CDCl$_3$) δ1.72(m, 2H, CH$_2$), 2.21(s, 6H, 2ArCH$_3$), 2.49(t, J=7 Hz, 2H, ArCH$_2$), 3.22(q, J=7 Hz, 2H, NCH$_2$), 3.47(s, 2H, CH$_2$CO), 3.87(s, 3H, OCH$_3$), 5.44 (s, 1H, NH), 5.78(s, 1H, OH), 6.68–7.04(m, 6H, ArH)

Step 4)

Synthesis of N-{3-(3,4-dimethylphenyl)propyl}-4-(2-hydroxyethoxy)-3-methoxyphenylacetamide To a solution containing 0.40 g (1.22 mmol) of the compound obtained in Step 3 and 2 ml of ethanol(99.9%) was added 0.80 (1.47 mmol) of potassium hydroxide. This mixture was stirred and 0.1 ml(1.47 mmol) of 2-chloroethanol was slowly added thereto. The mixture was refluxed for 5 hours and 20 ml of water was added thereto, extracted with 30 ml of dichloromethane, and the organic layer was dried. The solvent was evaporated under a reduced pressure and the residue was triturated with a mixture of dichloromethane and n-hexane(1:2) to obtain 0.25 g of the title compound as a white solid(yield: 56%).

m.p.: 119°–120° C.

$^1$H HNMR(200 MHz, CDCl$_3$) δ1.73(quint, 2H, J=7.3 Hz, CH$_2$), 2.22(s, 6H, 2CH$_3$), 2.50(t, 2H, J=7.7 Hz, ArCH$_2$), 3.22(q, 2H, J=6.7 Hz, NCH$_2$), 3.49(s, 2H, COCH$_2$), 3.85(s, 3H, OCH$_3$), 3.94(q, 2H, J=4.4 Hz, OCH$_2$), 4.13(t, 2H, J=4.5 Hz, OCH$_2$), 5.35(brs, 1H, NH), 6.73–7.02(m, 6H, ArH)

EXAMPLE 2

Synthesis of N-{3-(3,4-dimethylphenyl)propyl}-4-[2-{N-(2-hydroxyethyl)}aminoethoxy]-3-methoxy phenylacetamide Step 1)

Synthesis of N-{3-(3,4-dimethylphenyl)propyl}-4-(2-bromoethoxy)-3-methoxyphenylacetamide 1.80 g of the compound obtained in Step 3 of Example 1 was dissolved in a mixture of 60 ml of tetrahydrofuran and 10 ml of dibromoethane, and 2.2 g of 50% NaH was added thereto. The mixture was refluxed for 12 hours, and then poured into 200 ml of water. The resulting mixture was extracted twice with 150 ml of dichloromethane and the solvent was evaporated under a reduced pressure. The residue was subjected to column chromatography (eluent:ethyl acetate:n-hexane=1:1) and triturated with a mixture of dichloromethane and hexane(1:2) to obtain 1.53 g of the title compound as a white solid(yield: 63%).

m.p.: 105° C.

$^1$H NMR(200 MHz, CDCl$_3$) δ1.73(quint, 2H, J=7 Hz, CH$_2$), 2.21(s, 6H, 2ArCH$_2$), 2.50(t, 2H, J=7 Hz, ArCH$_2$), 3.22(q, 2H, J=7 Hz, NCH$_2$), 3.48(s, 2H, CH$_2$CO), 3.66(t, 2H, J=6 Hz, CH$_2$Br), 3.86(s, 3H, OCH$_3$), 4.32(t, 2H, J=6 Hz, OCH$_2$), 5.38(br s, 1H, NH), 6.73–7.05(m, 6H, ArH)

Step 2)

Synthesis of N-{3-(3,4-dimethylphenyl)propyl}-4-[2-{N-(2-hydroxyethyl) }aminoethoxy]-3-methoxyphenylacetamide 0.50 g (1.15 mmol) of the compound obtained in Step 1 was dissolved in 5 ml of acetonitrile and 0.13 g (1.27 mmol) of triethylamine and 0.35 g (5.76 mmol) of 2-ethanolamine were added thereto, which was refluxed for 6 hours. The reaction mixture was adjusted to pH 2–3 by using 1N aqueous HCl solution and the aqueous layer was separated from the organic layer. The aqueous layer was adjusted to pH 10–11, extracted with 50 ml of dichloromethane and dried. The solvent was distilled off under a reduced pressure and the residue was triturated with a mixture of dichloromethane and hexane(1:2) to obtain 0.16 g of the title compound as a white solid(yield: 94%).

m.p.: 76°–79° C.

$^1$H NMR(300 MHz, CDCl$_3$) δ1.76(quint, 2H, J=7.4 Hz, CH$_2$), 2.20(s, 6H, 2CH$_3$), 2.50(t, 2H, J=7.6 Hz, ArCH$_2$), 2.86(t, 2H, J=5.2 Hz, NCH$_2$), 3.10(t, 2H, J=5.2 Hz, CH$_2$N), 3.23(q, 2H, J=6.8 Hz, CONCH$_2$), 3.50(s, 2H, COCH$_2$), 3.68(t, 2H, J=5.2 Hz, OCH$_2$), 3.75(s, 3H, OCH$_3$), 4.13(t, 2H, J=5.2 Hz, OCH$_2$), 5.40(br s, 1H, NH), 6.72–7.05(m, 6H, ArH)

EXAMPLE 3

Synthesis of N-{3-(3,4-dimethylphenyl)propyl}-4-[2-{N,N-di(2-hydroxyethyl)}aminoethoxy]-3-methoxyphenylacetamide Step 1)

Synthesis of ethyl 4-(2-chloroethoxy)-3-methoxyphenylacetamide 46.4 g (0.216 mol) of ethyl homovanillate(ehtyl 4-hydroxy-3-methoxyphenylacetate) and 91.7 ml (1.08 mol) of 1-bromo-2-chloroethane were dissolved in 294 ml of acetone and 90.0 g (0.648 mol) of potassium carbonate was added thereto. The mixture was refluxed for 42 hours and 200 ml of water was added thereto, which was extracted with 500 ml of dichloromethane. The organic layer was washed successively with 100 ml of 0.1N aqueous NaCl solution and 100 ml of water; then the solvent was distilled off under a reduced pressure to obtain 51.7 g of the title compound as a yellow solid(yield: 88%).

m.p.: 51°–55° C.

$^1$H NMR(200 MHz, CDCl$_3$) δ1.26(t, 3H, J=7.2 Hz, CH$_2$), 3.56(s, 2H, ArCH$_2$), 3.85(t, 2H, J=6.2 Hz, CH$_2$Cl ), 3.87(s, 3H, OCH$_3$), 4.16(q, 2H, J=7.2 Hz, CO$_2$CH$_2$), 4.26(t, 2H, J=6.2 Hz, ArOCH$_2$), 6.70–6.84(m, 3H, ArH)

Step 2)

Synthesis of ethyl 4-(2-azidoethoxy)-3-methoxyphenylacetate 51.0 g (0.187 mol) of the compound obtained in step 1 was dissolved in 500 ml of toluene and then 61.4 g (0.935 mol) of NaN$_3$, 12.1 g (37 mmol) of n-Bu$_4$NBr and 3.16 g (0.186 mol) of potassium iodide were added thereto. The resulting mixture was refluxed for 6 hours and 500 ml of dichloromethane was added thereto. The solution thus obtained was successively washed with 200 ml of water, 100 ml of 0.1N aqueous NaCl solution and 100 ml of water. The solvent was distilled off under a reduced pressure to obtain 52.3 g of the title compound as a sticky liquid(yield: 100%).

Step 3)

Synthesis of 4-(2-azidoethoxy)-3-methoxyphenylacetic acid

A mixture of 15.03 g (53.8 mmol) of the compound obtained in Step 2, 6 g (0.16 mmol) of sodium chloride and 80 of water was refluxed for 2 hours and ethanol was distilled off under reduced pressure. The residue was washed with 60 ml of dichloromethane. The aqueous layer was adjusted to pH 2–3 with 1N aqueous HCl solution and extracted with 200 ml of dichloromethane. The solvent was distilled off under a reduced pressure to obtain 11.83 g of the title compound as a yellow solid (yield: 87%).

$^1$H NMR(200 MHz, CDCl$_3$) δ3.60(s, 2H, ArCH$_2$), 3.65(t, 2H, J=5.2 Hz, CH$_2$N$_3$), 3.86(s, 3H, OCH$_3$), 4.17(q, 2H, J=5.2 Hz, ArOCH$_2$), 6.85(m, 3H, ArH)

Step 4)

Synthesis of N-{3-(3,4-dimethylphenyl)propyl}-4-(2-azidoethoxy)-3-methoxyphenylacetamide 11.5 g (46.0 mmol) of the compound obtained in Step 3 and 4.2 ml (55 mmol) of thionyl chloride were refluxed in 120 ml of dichloromethane for 2 hours. The solvent and excess thionyl chloride were removed under a reduced pressure and the residue was dissolved in 100 ml of dichloromethane. The resultant solution was added dropwise to a solution containing 7.10 g (43.5 mmol) of the compound obtained in Step 2 of Example 1 and 20 ml of dichloromethane over 2 hours, followed by stirring for 12 hours at room temperature. The reaction mixture was successively washed with 50 ml of 1N HCl, 50 ml of 1N aqueous NaCl solution and 50 ml of water and the solvent was distilled off under a reduced pressure. The residue was recrystallized from isopropanol to obtain 7.7 g of the title compound as a yellow solid(yield: 51%).

m.p.: 101°–103° C.

$^1$H NMR(200 MHz, CDCl$_3$) δ1.73(tt, 2H, J=7.9, 7.2 Hz, CH$_2$), 2.2(s, 6H, 2CH$_3$), 2.50(t, 2H, J=7.8 Hz, ArCH$_2$), 3.22(dt, 2H, J=7.0, 6.2 Hz, NHCH$_2$), 3.49(s, 2H, ArCH$_2$CO), 3.64(t, 2H, J=5.4 Hz, CH$_2$N$_3$), 3.85(s, 3H, OCH$_3$), 4.18(t, 2H, J=5.4 Hz, ArOCH$_2$), 5.35(br s, 1H, NH), 6.71–7.04(m, 6H, ArH)

Step 5 )

Synthesis of N-{3-(3,4-dimethylphenyl)propyl}-4-(2-aminoethoxy)-3-methoxyphenylacetamide 1.00 g (2.52 mmol) of the compound obtained in Step 4 was dissolved in 100 ml of ethyl acetate and 0.30 g of 10% Pd-C was added thereto, which was reacted under a hydrogen atmosphere of about 40 psi for 5 hours. The reaction mixture was filtered through Celite to remove Pd/C, the solvent was distilled off under a reduced pressure and the residue was recrystallized from dichloromethane/hexane to obtain 0.88 g of the title compound (yield: 94%).

m.p.: 125° C.

$^1$H NMR(200 MHz, CDCl$_3$) δ1.72(m, 4H, CH$_2$, NH$_2$), 2.21(s, 6H, 2ArCH$_3$), 2.49(t, 2H, J=7 Hz, ArCH$_2$), 3.11(q, 2H, J=5 Hz, OCH$_2$), 3.22(q, 2H, J=7 Hz, NCH$_2$), 3.49(s, 2H, CH$_2$CO), 3.85(s, 3H, OCH$_3$), 4.04(t, 2H, J=5 Hz, CH$_2$N), 5.42(br s, 1H, NH), 6.71–7.03(m, 6H, ArH)

Step 6)

Synthesis of N-{3-(3,4-dimethylphenyl)propyl}-4-[2-{N,N-di(2-hydroxyethyl)}aminoethoxy]-3-methoxyphenylacetamide 0.12 g (0.31 mmol) of the compound obtained in Step 5 was dissolved in 30 ml of acetonitrile and 0.2 g (3 mmol) of 2-bromoethanol and 0.3 ml(2 mmol) of triethylamine were added thereto, and the resulting mixture was refluxed for 12 hours. After the completion of the reaction, the procedure in Step 2 of Example 2 was repeated to obtain 0.09 g of the title compound (yield: 60%).

m.p.: 54°–58° C.

¹H NMR(200 MHz, CDCl₃) δ1.65–1.80(m, 2H, CH₂N), 2.21(s, 6H, 2CH₃2.50(t, 2H, J=7.5 Hz, ArCH₂), 2.75(t, 4H, J=4.7 Hz, NCH₂), 2.98(t, 2H, J=4.8 Hz, NCH₂), 3.16–3.27 (m, 2H, CH₂N), 3.47(s, 2H, CH₂Ar), 3.61(t, 4H, J=4.7 Hz, OCH₂), 3.83(s, 3H, OCH₃), 4.03(t, 2H, J=4.8 Hz, CH₂OAr), 5.48(br s, 1H, NH), 6.71–7.03(m, 6H, ArH)

EXAMPLE 4

Synthesis of N-{3-(3,4-dimethylphenyl)propyl}-4-[2-{N-(2-aminoethyl)}aminoethoxy]-3-methoxyphenylacetamide 0.35 g (0.81 mmol) of N-{3-(3,4-dimethylphenyl) propyl}-4-(2-bromoethoxy)-3-methoxyphenylacetamide obtained in step 1 of Example 2 was dissolved in 3 ml of dimethylsulfoxide and 0.56 g (4.02 mmol) of potassium carbonate was added thereto. To this mixture, 0.48 g (8.06 mmol) of ethylenediamine was slowly added at room temperature, followed by stirring at room temperature for 4 hours. The reaction mixture was diluted with 40 ml of dichloromethane, washed with water and acidified with 1N HCl and the aqueous layer was separated. The aqueous layer was basified with hydrogen peroxide, extracted with 40 ml of dichloromethane, dried and the solvent was removed under a reduced pressure. The residue was triturated with a mixture of dichloromethane and hexane(1:2) to obtain 0.10 g of the title compound as a white solid(yield: 30%).

m.p.: 119°–120° C.

¹H NMR(200 MHz, CDCl₃) δ1.72(q, 2H, J=6.9 Hz, CH₂), 2.24(s, 6H, 2CH₃), 2.52(t, 2H, J=7.5 Hz, CH₂Ar), 2.81(q, 4H, J=5.3 Hz, CH₂NH), 3.08(t, 2H, J=5.5 Hz, CH₃NH₂), 3.25(q, 2H, J=6.7 Hz, NHCH₂), 3.51(s, 2H, CH₂CO), 3.80(s, 3H, OCH₃), 4.15(t, 2H, J=5.3 Hz, OCH₂), 5.39(brs, 1H, NH), 6.73–7.07(m, 6H, ArH)

EXAMPLE 5

Synthesis of N-{3-(3,4-dimethylphenyl)propyl}-4-(2-piperazinylethoxy)-3-methoxyphenylacetamide The procedure of Example 4 was repeated except that piperazine was used in place of ethylenediamine to obtain 0.27 g of the title compound as a white solid(yield: 77%).

m.p.: 92°–94° C.

¹H NMR(200 MHz, CDCl₃) δ1.72(q, 2H, J=6.7 Hz, CH₂), 2.22(s, 6H, 2CH₃), 2.47–2.62(m, 6H, 3CH₂), 2.82–2.97(m, 6H, N(CH₂)₃), 3.22(q 2H, J=6.9 Hz, amide-CH₂), 3.49(s, 2H, CH₂CO), 3.86(s, 3H, OCH₃), 4.15(t, 2H, J=6.1 Hz, OCH₂), 5.40(brs, 1H, NH), 6.72–7.05(m, 6H, ArH)

EXAMPLE 6

Synthesis of N-{3-(3,4-dimethylphenyl)propyl}-4-(2-ethylformamido)-3-methoxyphenyl-acetamide 0.15 ml (3.93 mmol) of formic acid was slowly added to 0.33 g (3.19 mmol) of acetic acid anhydride at 0° C. After 10 minutes, the mixture was heated to the temperature ranging from 50° to 60° C. and then stirred for 2 hours. To the mixture were added 1 ml of dry tetrahydrofuran at room temperature and 0.45 g (1.2 mmol) of N-{3-(3,4-dimethylphenyl)propyl}-4-(2-aminoethoxy)-3-methoxyphenylacetamide obtained Step 5 of Example 3 at −20° C. and the whole mixture was stirred for 3 hours at room temperature. After removing the solvent under a reduced pressure, the residue was subjected to column chromatography (eluent: ethyl acetate: hexane=1:1) to recover 0.11 g of the starting material and to obtain 0.24 g of the title compound as a white solid(yield: 62%).

m.p.: 109°–111° C.

¹H NMR(200 MHz, CDCl₃) δ1.75(q, 2H, J=7.4 Hz, CH₂), 2.23(s, 6H, 2CH₃), 2.52(t, 2H, J=7.6 Hz, ArCH₂), 3.25(q, 2H, J=6.8 Hz, NCH₂), 3.50(s, 2H, COCH₂), 3.73(q, 2H, J=5.2 Hz, NCH₂), 3.87(s, 3H, OCH₃), 4.12(t, 2H, J=5.0 Hz, OCH₂), 5.39(br s, 1H, NH), 6.28(brs, 1H, NH), 6.73–7.05 (m, 6H, ArH), 8.24(s, 1H, CHO)

EXAMPLE 7

Synthesis of N-{3-(3,4-dimethylphenyl)propyl}-4-{2-(N-benzyloxycarbonyl)aminoethoxy}-3-methoxyphenylacetamide 2.05 g (5.0 mmol) of N-{3-(3,4-dimethylphenyl)propyl}-4-(2-aminoethoxy)-3-methoxyphenylacetamide obtained in Step 5 of Example 3 was dissolved in 50 ml of dichloromethane and 2.2 ml (15 mmol) of triethylamine was added thereto. The mixture was stirred at 0° C. and 1.03 g (6.0 mmol) of benzylchloroformate was slowly added thereto while maintaining the temperature at 0° C. The resultant solution was stirred for 2 hours and the reaction mixture was washed with water. The organic layer was dried and the solvent was distilled off under a reduced pressure. The residue was subjected to silica gel column chromatography (eluent: ethyl acetate:hexane=1:1) to obtain 2.48 g of the title compound as a white solid(yield: 98%).

m.p.: 110°–112° C.

¹HNMR(200MHZ, CDCl₃) δ1.72(quint, 2H, J=7.5 Hz, CH2), 2.20(s, 6H, 2CH₃), 2.48(t, 2H, J=7.4 Hz, ArCH₂), 3.2(m, 2H, CH₂), 3.47(s, 2H, COCH₂), 3.61 (q, 2H, J=5.2 Hz, NCH₂), 3.81(s, 3H, OCH₃), 4.08(t, 2H, J=5.2 Hz, OCH₂), 5.10(s, 2H, CH₂), 5.38(brs, 1H, NH), 5.40(br s, 1H, NH), 6.69–6.87(m, 4H, ArH), 7.01(d, J=7.4 Hz, 1H, ArH), 7.31–7.37(m, 6H, ArH)

EXAMPLE 8

Synthesis of N-{3-(3,4-dimethylphenyl)propyl}-4-(2-methylaminoethoxy)-3-methoxyphenylacetamide 0.10 g (0.23 mmol) of N-{3-(3,4-dimethylphenyl) propyl}-4-(2-bromoethoxy)-3-methoxyphenylacetamide obtained in step 1 of Example 2 and a catalytic amount of dimethylaminopyridine were dissolved in 50 ml of tetrahydrofuran and 0.048 g (0.35 mmol) of potassium carbonate was added thereto. Then, methylamine was passed through the mixture by bubbling at the temperature ranging from −10° to −20° C. The resultant mixture was stirred at a room temperature for 6 hours. After removing the solvent under a reduced pressure, the residue was subjected to silica gel column chromatography(eluent: ethyl acetate:hexane=1:1) to obtain the title compound.

EXAMPLE 9

Synthesis of N-{3-(3,4-dimethylphenyl)propyl}-4-{2-(1-pyrrolidinyl)ethoxy}-3-methoxyphenylacetamide 0.10 g (0.23 mmol) of N-{3-(3,4-dimethylphenyl) propyl}-4-(2-bromoethoxy)-3-methoxyphenylacetamide obtained in Step 5 of Example 3, 0.16 g (2.3 mmol) of pyrrolidine and a catalytic amount of dimethylaminopyridine were dissolved in 10 ml of benzene, and the mixture was refluxed for 5 hours. After removing the solvent under a reduced pressure, the residue was subjected to silica gel column chromatography (eluent: ethyl acetate:hexane=1:1) to obtain the title compound.

$^1$H NMR(300 MHz, CDCl$_3$) δ1.73(quint, 2H, J=7.2 Hz, CH$_2$) 2.21(s, 6H, 2CH$_3$), 2.47–2.67(m, 10H, 5CH$_2$), 2.94(t, 2H, J=6.4 Hz, NCH$_2$), 3.21(q, 2H, J=6.3 Hz, CH$_2$), 3.47(s, 2H, COCH$_2$), 3.84(s, 3H, OCH$_3$), 4.14(t, 2H, J=6.3 Hz, OCH$_2$), 5.74(brs, 1H, NH), 6.74–7.03(m, 6H, ArH)

EXAMPLE 10

Synthesis of N-{3-(3,4-dimethylphenyl)propyl}-4-{2-(N-ethyloxycarbonyl)aminoethoxy}-3-methoxyphenylacetamide 0.80 g (2.2 mmol) of N-{3-(3,4-dimethylphenyl)propyl}-4-(2-aminoethoxy)-3-methoxyphenylacetamide obtained in Step 5 of Example 3, was dissolved in 30 ml of dichloromethane and 0.26 g (2.6 mmol) of trimethylamine was added thereto. This mixture was stirred at 0° C. and 0.18 ml (2.4 mmol) of ethyl chloroformate was slowly added thereto, which was stirred for 2 hours while maintaining the temperature at 0° C. The reaction mixture was washed with water and extracted with 40 ml of dichloromethane. The organic layer was dried and the solvent was removed under a reduced pressure. The residue was subjected to silica gel chromatography and triturated with a mixture of dichloromethane and hexane(1:2) to obtain 0.74 g of the title compound as a white solid(yield: 80%).

m.p.: 124°–125° C.

$^1$H NMR(200 MHz, CDCl$_3$) δ1.73(quint, 2H, J=7.5 Hz, CH$_2$), 2.21(s, 6H, 2CH$_3$), 2.50(t, 2H, J=7.7 Hz, ArCH$_2$), 3.22(q, 2H, J=6.8 Hz, NCH$_2$), 3.48(s, 2H, COCH$_2$), 3.60(q, 2H, J=5.2 Hz, NCH$_2$), 3.69(s, 3H, OCH$_3$), 3.85(s, 3H, OCH$_3$), 4.07(t, 2H, J=5.2 Hz, OCH$_2$), 5.38(brs, 1H, NH), 6.70–7.04(m, 6H, ArH)

EXAMPLE 11

Synthesis of N-{3-(3,4-dimethylphenyl)propyl }-4-[2-{N-(2-acetoxybenzoyl)}aminoethoxy]-3-methoxyphenylacetamide 0.27 g (0.66 mmol) of N-{3-(3,4-dimethylphenyl)propyl}-4-(2-aminoethoxy)-3-methoxyphenylacetamide obtained in Step 5 of Example 3, 0.17 g (0.94 mmol) of acetylsalicylic acid and 0.10 g (0.74 mmol) of 1-hydroxylbenzotriazole were dissolved in 15 ml of a mixture of acetonitrile and dimethylformamide(1:2). 0.19 g (0.92 mmol) of dicyclohexanecarbodiimide was added thereto and the resultant mixture was stirred at a room temperature for 2 days. White precipitates were removed and the remaining solution was diluted with 30 ml of dichloromethane, which was washed with water and dried. After removing the solvent under a reduced pressure, the residue was subjected to silica gel chromatography to obtain 0.22 g of the title compound (yield: 63%).

m.p.: 135°–137° C.

$^1$H NMR(200 MHz, CDCl$_3$) δ1.71(quint, J=7.3 Hz, 2H, CH$_2$), 1.98(s, 3H, CH$_3$), 2.19(s, 6H, 2CH$_3$), 2.48(t, J=7.5 Hz, 2H, CH$_2$Ar), 3.20(q, J=7.5 Hz, 2H, NCH$_2$), 3.45(s, 2H, CH$_2$CO), 3.63(q, J=5.1 Hz, 2H, NCH$_2$), 3.83(s, 3H, OCH$_3$), 4.05(t, J=5.0 Hz, 2H, OCH$_2$), 5.46(brs, 1H, NH), 6.25(brs, 1H, NH), 6.69–7.01(m, 10H, ArH)

ACTIVITY TEST

Physiological activities of the compounds obtained in Examples 1 to 11 were measured by employing acetic acid or phenyl-1,4-benzoquinone(PBQ) induced writhing test.

1) Animals tested

The KTC-ICR mice provided by Experimental Animal Laboratory of Korea Research Institute of Chemical Technology were used as test animals. The mice subjected to the acetic acid induced writhing test had a body weight ranging from 20 to 25 g; and those subjected to the PBQ induced writhing test had a body weight ranging from 14 to 18 g. They were tested in a group consisting of 8 mice for each dosage of a test compound after having been adjusted to the testing environment for a week. Food and water were given freely; and illumination was maintained on a 12-hour cycle.

2) Testing method

Test solutions were prepared by dissolving one of the final products obtained in Examples 1 to 11 in distilled water containing 1% of Tween and 5% ethanol in a pre-determined concentration. The test solutions were used after serial dilution depending on each dosage.

The test solutions were intraperitoneally administered in a dose of 0.1 ml per 10 g of a body weight. 0.1 ml of 1% acetic acid solution or 0.1 ml of 0.02% PBQ solution was administered after 60 minutes in case of oral administration or after 30 minutes in case of subcutaneous injection.

Then, the number of writhings generated during a period of 10 minutes after 3 minutes from the administration of acetic acid was measured. In case of the administration of PBQ, the number of writhings generated during a period of 5 minutes after 5 minutes from the administration was measured.

For a comparison purpose, initially, distilled water containing 1% of Tween and 5% ethanol alone was administered to the control group. Then, the control groups were subjected to the same procedure as the test groups.

3) Measurement of analgesic effect

The number of writhings suffered by the test group was compared with that of the control group; and the analgesic effect was measured in terms of the percentage of inhibition of writhing(I. W.).

$$I.\ W.\ (\%) = \frac{A-B}{A} \times 100$$

wherein:

A is the number of writhings suffered by the control group; and

B is the number of writhings suffered by the test group.

I.W. values for each dosage were calculated by employing regression analysis. The amount of a test compound which is required in reducing the frequency of writhings to the 50% level of that generated by the control group, i.e., B=0.5A or I.W.=50%, is designated as ED$_{50}$(mg/kg of a body weight). Therefore, a lower value of ED$_{50}$ represents a higher analgesic effect of the tested compound. These ED$_{50}$ values for the test compounds are shown in Table I.

TABLE I

| Compounds | ED$_{50}$ (mg/kg of a body weight) | |
|---|---|---|
| | acetic acid | PBQ |
| NE-19550[1] | 15.7 | |
| NE-21610[2] | >300 | 38.3 |
| Capsaicin[3] | 1.34 | |
| Phenylbutazone[4] | | 79.8 |
| Aspirin[5] | | 71.4 |
| Naproxen[6] | | 17.1 |
| Ibuprofen[7] | | 11.0 |

TABLE I-continued

|  | ED$_{50}$ (mg/kg of a body weight) | |
|---|---|---|
| Compounds | acetic acid | PBQ |
| Example 1 | 2.01 | |
| Example 2 | 0.30 | 0.83 |
| Example 3 | 1.41 | |
| Example 4 | 1.78 | |
| Example 5 | >20 | |
| Example 6 | 0.26 | |
| Example 7 | 1.51 | |
| Example 8 | | 0.68 |
| Example 9 | >5 | |
| Example 10 | >10 | |
| Example 11 | 4.15 | |

Notes: [1] N-vanillyloleamide (see EP 0 282 127)
[2] N-{4-(2-aminoethoxy)-3-methoxybenzyl}-oleamide (see EP 0 282 127)
[3] N-vanillyl-trans-8-methyl-6-nonenamide
[4]–[7] commercially available antiphlogistic analgesia

TOXICITY TEST

In order to monitor a harmful side-effect or toxicity of the present compounds, various behavioral changes in the test animals were observed. After the test and the control solutions were administered to the animals, symptoms such as sedation, ptosis, dyspnoea, vasodilation, convulsion, salivation and urination were observed by the naked eye and the level of such changes was represented by a numbering system: that is, the normal value of the last three behaviors (i.e., urination, convulsion and salivation) is 0; and that of the others (i.e., sedation, ptosis, dyspnoea and vasodilation) is 4. The higher the number is, the greater the side effects are.

The results of the test for some of the compounds are shown in Table II.

TABLE II

| | Compounds | | | | | | | |
|---|---|---|---|---|---|---|---|---|
| Ex. | Amount mg/kg | Sedation | Ptosis | Dyspnoea | Vasodilation | Convulsion | Salivation | Urination |
| 1 | 4 | 6 | 5 | 5 | 5 | 0 | 0 | 0 |
| | 2 | 4 | 4 | 4 | 4 | 0 | 0 | 0 |
| | 1 | 4 | 4 | 4 | 4 | 0 | 0 | 0 |
| 2 | 1 | 6 | 6 | 5 | 5 | 0 | 0 | 0 |
| | 0.5 | 5 | 5 | 4 | 4 | 0 | 0 | 0 |
| | 0.25 | 4 | 4 | 4 | 4 | 0 | 0 | 0 |
| 3 | 5 | 6 | 7 | 6 | 5 | 0 | 0 | 0 |
| | 2.5 | 5 | 5 | 4 | 4 | 0 | 0 | 0 |
| | 1.25 | 4 | 4 | 4 | 4 | 0 | 0 | 0 |
| 5 | 4 | 6 | 6 | 4 | 4 | 0 | 0 | 0 |
| | 2 | 4 | 4 | 4 | 4 | 0 | 0 | 0 |
| | 1 | 4 | 4 | 4 | 4 | 0 | 0 | 0 |
| Con- | 1 | 7 | 7 | 6 | 6 | 1 | 0 | 0 |
| trol* | 0.5 | 7 | 7 | 6 | 5 | 1 | 0 | 0 |
| | 0.25 | 6 | 6 | 5 | 5 | 1 | 0 | 0 |
| | 0.2 | 4 | 4 | 4 | 4 | 1 | 0 | 0 |

*Control compound: N-{3-(3,4-dimethylphenyl)propyl}-4-(2-aminoethoxy)-3-methoxyphenylacetamide (see U. S. Pat. No. 5,242,944)

While the invention has been described with respect to the specific embodiments, it should be recognized that various modifications and changes may be made by those skilled in the art to the invention which also fall within the scope of the invention as defined by the appended claims.

What is claimed is:

1. A N-arylalkylphenylacetamide compound of formula (I) and pharmaceutically acceptable salts thereof:

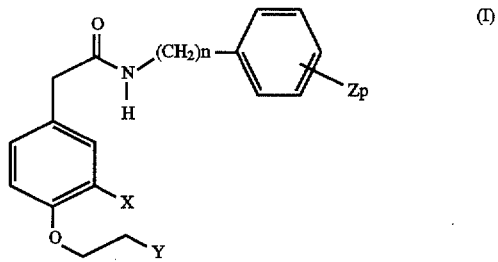

wherein:

X is hydroxy or methoxy;

Y is hydroxy; or NR$^1$R$^2$ wherein R$^1$ and R$^2$, which may be the same or different, are independently hydrogen, C$_{1-3}$ alkyl, C$_{1-3}$ hydroxyalkyl, C$_{1-3}$ aminoalkyl, formyl, C$_{1-3}$ alkylcarbonyl, C$_{1-3}$ alkoxycarbonyl, arylalkoxycarbonyl, aryl, or aroyl, with the proviso that both R$^1$ and R$^2$ are not simultaneously hydrogen, or R$^1$ and R$^2$ may form a heterocyclic ring containing one or more heteroatoms together with the nitrogen atom to which they are attached;

Z, which may be the same or different when p is greater than 1, is hydrogen, halogen, methylenedioxy, trifluoromethyl, or C$_{1-5}$ alkyl;

n is an integer ranging from 2 to 4; and p is an integer ranging from 1 to 5.

2. The compound of claim 1, wherein n is 3, p is 2 and X is methoxy, and pharmaceutically acceptable salts thereof.

3. The compound of claim 2, wherein Y is NR$^1$R$^2$ wherein R$^1$ and R$^2$ are independently hydrogen, C$_{1-3}$ hydroalkyl or C$_{1-3}$ aminoalkyl, with the proviso that both R$^1$ and R$^2$ are not simultaneously hydrogen, and pharmaceutically acceptable salts thereof.

4. A pharmaceutical composition comprising an effective amount of the compound recited in claim 1 as an active ingredient, and a pharmaceutically acceptable carrier or adjuvant.

* * * * *